US00PP09574P

United States Patent [19]

Olij

[11] Patent Number: Plant 9,574

[45] Date of Patent: Jun. 11, 1996

[54] HYBRID TEA ROSE PLANT NAMED 'OLIJFAON'

[75] Inventor: Huibert W. Olij, De Kwakel, Netherlands

[73] Assignee: The Conard-Pyle Company, West Grove, Pa.

[21] Appl. No.: 543,974

[22] Filed: Oct. 17, 1995

[51] Int. Cl.[6] ..... A01H 5/00

[52] U.S. Cl. ..... Plt./11

[58] Field of Search ..... Plt./11–14

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive long-lasting blossoms that are white edged with pink. The plant exhibits an erect growth habit and strong vegetation. The new variety exhibits very good disease resistance and is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characterisitcs. The female parent (i.e., the seed parent) of the new variety was the 'Laminuette' variety (U.S. Plant Pat. No. 3,162). The 'Laminuette' variety sometimes is known as the 'Minuette' variety. The male parent (i.e., the pollen parent) was the 'Nicole' variety (non-patented in the United States). The parentage of the new variety can be summarized as follows:

'Laminuette'×'Nicole'.

The seeds resulting from the above pollination were sown and 33 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive bicolored blossoms that are white edged with pink,
(b) exhibits an erect growth habit,
(c) is well suited for cut flower production under greenhouse growing conditions, and
(d) exhibits good disease resistance.

The new variety well meets the needs of the horticultural industry and is particularly well suited for the commercial production of cut flowers when grown indoors.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Olijfaon' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouse at Le Cannet des Maures, Var, France.

DETAILED DESCRIPTION

Figures 1, 2, 3, 4, 5, 6, 7, 8, 9, 10, 11, 12, 13, 14, 15:
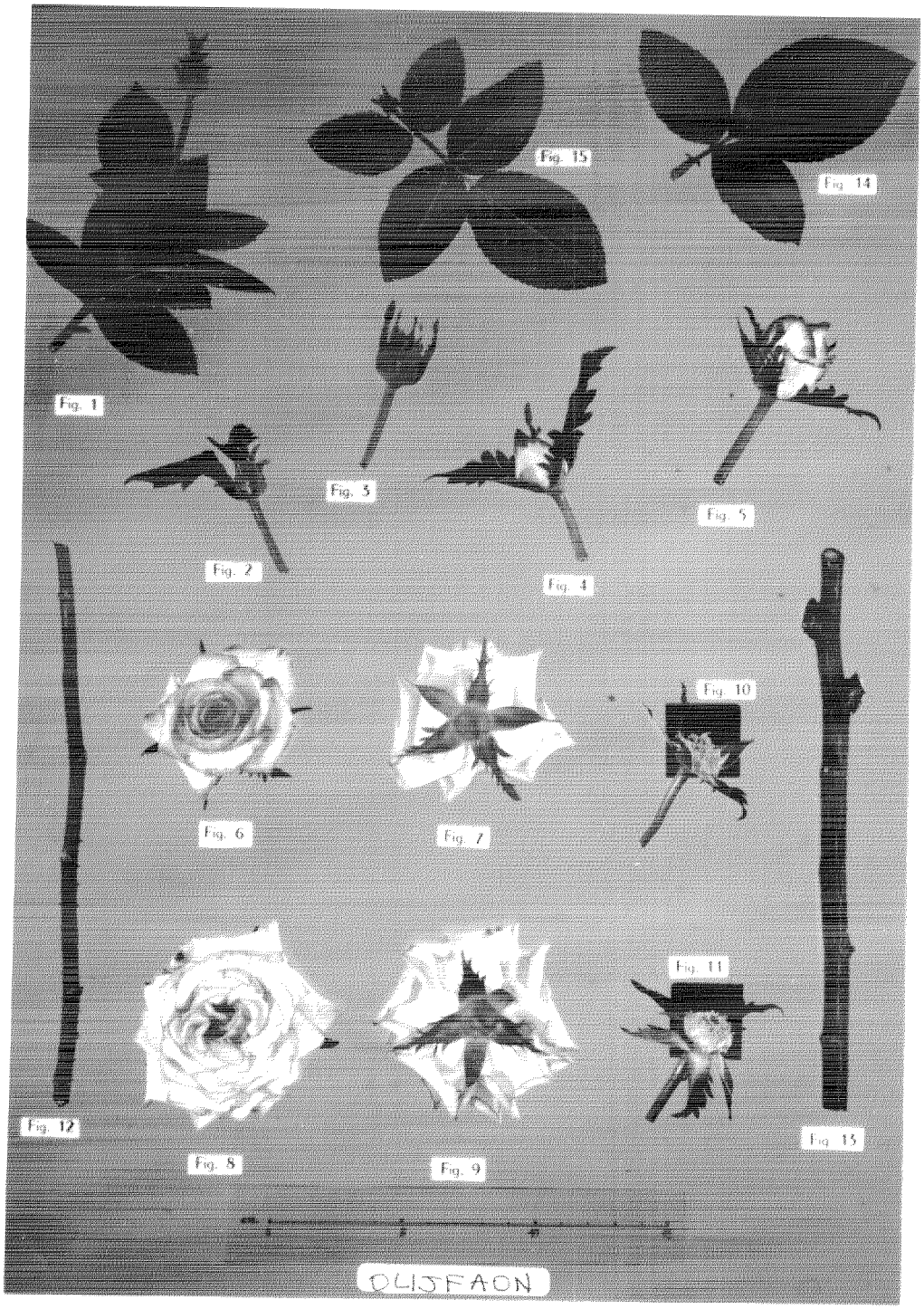
FIG. 1 illustrates a specimen of a young shoot with bud.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — under surface.

The chart used in the identification of the colors is that of The Royal Horticultural Society (R.H.S. Colour Chart). The description is based on the observation during September of three year-old plants while budded on *Rosa indica* understock and growing in greenhouse at Le Cannet de Maures, Var. France. The coloration in common terms precedes reference to the chart.

Class: Hybrid Tea.

Plant:

*Height.*—Approximately 50 to 60 cm. on average at the end of the growing season.

*Habit.*—Erect.

Branches:

*Color.*—Young stems: medium green, Green Group 143B. Adult wood: medium green, Green Group 137B, and sometimes suffused with reddish coloration.

*Thorns.*—Size: very small. Quantity: very few. Color: generally greenish.

Leaves:

*Stipules.*—Adnate, pectinate, broad and linear.

*Petioles.*—Upper surface: striped reddish on young foliage and medium green on adult foliage with glandular edges. Under surface: light green.

*Leaflets.*—Number: commonly 3, 5 (most often), and 7. Shape: elliptic. Serration: single and regular. Texture: consistent. General appearance: dense, medium green, and semi-bright. Color (young foliage): Upper surface: dark green, Yellow-Green Group 147A. Under surface: medium green, Green Group 137C. Color (adult foliage): Upper surface: dark green, Green group 139A. Under surface: medium green, Green Group 138A.

Inflorescence:

*Number of flowers.*—Usually one to three per stem.

*Peduncle.*—Medium green in coloration and smooth. The length is approximately 8 to 10 cm. on average.

*Sepals.*—Upper surface: tomentose, and greenish in coloration. Under surface: medium green in coloration and the edges commonly are appendiculated.

*Buds.*—Shape: conical. Length: approximately 2.5 to 3 cm. on average. Size: medium. Color upon opening: Upper surface: Mimosa Yellow, Yellow Group 8D, and edged with Cardinal Red, Red Group 53B. Under surface: Chrome Yellow, Yellow-White Group 158C edged with Cardinal Red, Red Group 53B, and lightly suffused with Azalea Pink, Red Group 38B.

*Flower.*—Shape: cupped with a high center. Diameter: approximately 11 to 12 cm. on average. Color (when opening begins): Upper surface: white, White Group 155B and edged with Cardinal Red, Red Group 53B. Under surface: white, White Group 155B and edged with Cardinal Red, Red Group 53B. Color (when blooming): Upper surface: white, White Group 155B and edged with Cardinal Red, Red Group 53B. Under surface: white, White Group 155B and edged with Cardinal Red, Red Group 53B. Color (at end of opening): Upper surface: white, White Group 155B edged and suffused with Neyron Pink, Red Group 55A. Under surface: white, White Group 155B edged and suffused with Neyron Pink, Red Group 55B. Fragrance: none. Lasting quality: good. Petal shape: oval at the tip and obtuse at the base. Petal drop: good. Stamen number: approximately 190 on average. Anthers: normal golden yellow in coloration. Filaments: yellowish in coloration. Pistils: approximately 160 on average. Stigmas: yellowish in coloration. Styles: greenish in coloration. Receptacle: medium green, smooth, and in longitudinal section in the shape of a wide funnel.

Development:

*Vegetation.*—Strong.

*Blooming.*—Abundant.

*Resistance to disease.*—Good.

I claim:

1. A new and distinct variety of Hybrid Tea rose plant characterized by the following combination of characteristics:

(a) forms in abundance attractive bicolored blossoms that are white edged with pink,
(b) exhibits an erect growth habit,
(c) is well suited for cut flower production under greenhouse growing conditions, and
(d) exhibits good disease resistance;

substantially as herein shown and described.

* * * * *

OLIJFAON